US008731680B2

(12) United States Patent
Reinke et al.

(10) Patent No.: US 8,731,680 B2
(45) Date of Patent: May 20, 2014

(54) THERAPEUTIC UNIT AND THERAPEUTIC SYSTEM SUPPORTING A FOLLOW-UP EXAMINATION

(75) Inventors: Joachim Reinke, Berlin (DE); Joern Bungartz, Berlin (DE); Volker Kukla, Berlin (DE); Tobias Rau, Berlin (DE)

(73) Assignee: Biotronik CRM Patent AG, Baar (CH)

( * ) Notice: Subject to any disclaimer, the term of this patent is extended or adjusted under 35 U.S.C. 154(b) by 1213 days.

(21) Appl. No.: 12/104,385

(22) Filed: Apr. 16, 2008

(65) Prior Publication Data
US 2008/0262572 A1 Oct. 23, 2008

(30) Foreign Application Priority Data

Apr. 21, 2007 (DE) .......................... 10 2007 018 982

(51) Int. Cl.
*A61N 1/00* (2006.01)
(52) U.S. Cl.
CPC ........................................ *A61N 1/00* (2013.01)
USPC ............................................................. 607/60
(58) Field of Classification Search
CPC .............. A61B 5/00; A61B 5/02; A61B 5/03; A61B 5/04; A61B 5/07; A61B 5/08; A61B 5/22; A61B 5/0002; A61B 5/0033; A61B 5/0048; A61N 1/02; A61N 1/08; A61N 1/10; A61N 1/11; A61N 1/12; A61N 1/13; A61N 1/14; A61N 1/15; A61N 1/16; A61N 1/18; A61N 1/025; A61N 1/362; A61N 1/372; A61N 1/3605; A61M 21/00; A61M 1/12
See application file for complete search history.

(56) References Cited

U.S. PATENT DOCUMENTS

| | | | |
|---|---|---|---|
| 5,720,770 A | 2/1998 | Nappholz et al. | |
| 2003/0069751 A1 | 4/2003 | Lichtenstein et al. | |
| 2003/0119568 A1 | 6/2003 | Menard | |
| 2005/0283198 A1 | 12/2005 | Haubrich et al. | |
| 2006/0229053 A1 * | 10/2006 | Sivard | 455/343.2 |

FOREIGN PATENT DOCUMENTS

| | | |
|---|---|---|
| DE | 19930240 | 12/2000 |
| DE | 19930263 | 12/2000 |
| FR | 2 884 151 | 10/2006 |

OTHER PUBLICATIONS

German Search Report, dated Feb. 12, 2008.
European Search Report, dated Aug. 4, 2009.

* cited by examiner

*Primary Examiner* — Christopher D Koharski
*Assistant Examiner* — Elizabeth K So
(74) *Attorney, Agent, or Firm* — ARC IP Law, PC; Joseph J. Mayo

(57) ABSTRACT

Therapeutic system with implantable therapeutic unit (ITU) comprising control unit (CU), memory, telemetry unit connected (in)directly to CU for wireless bidirectional transmission of data to/from external device (ED) and detection unit for detecting physiological patient data or operational data. CU triggers outgoing data transmission (DT) from ITU to ED based on preselected internal events and establishes standby mode for reception on part of telemetry unit for receiving beginning (header) of incoming DT from ED to therapeutic unit exclusively within preselected response time window after DT from ITU to ED. System designed to add to incoming DT follow-up signaling data which signals an imminent follow-up examination, whereby CU also prompts sensor unit at preselected time point in response to receipt of follow-up signaling data to detect preselected physiological data required for follow-up examination or to detect operational data of therapeutic and store in memory and transmit with subsequent outgoing DT to ED.

10 Claims, 3 Drawing Sheets

THERAPEUTIC UNIT AND THERAPEUTIC SYSTEM SUPPORTING A FOLLOW-UP EXAMINATION

BACKGROUND OF THE INVENTION

1. Field of the Invention

The invention relates to a therapeutic system having an implantable therapeutic unit, e.g., an implantable medical device such as a cardiac pacemaker or a cardioverter/defibrillator.

2. Description of the Related Art

Implantable medical devices such as therapeutic units may be equipped with a bidirectional telemetry unit to be able in this way to communicate with a central remote service center via an external device near the patient (patient device). A physician treating the respective patient has patient-specific access to the service center and can retrieve physiological or implant-specific data, for example, from the service center after it has previously been sent from the therapeutic unit via the patient device to the service center.

BRIEF SUMMARY OF THE INVENTION

Wireless data transmission from the implantable medical device to the patient device also requires energy to be consumed on the part of the implantable medical device, said energy being made available only to a limited extent by a battery in an implantable medical device, so the bidirectional data communication between the implantable medical device and the patient device is usually limited. For example, it is provided here that the implantable medical device triggers an outgoing data transmission only when this is stipulated at certain times or when this is indicated by a particular event, e.g., an acute fibrillation detected on the part of the implantable medical device.

To save on energy, there are plans for the implantable medical device not to be continuously on standby for reception. Instead, the implantable medical device maintains its standby mode for reception for a response window for only a short period of time after conclusion of an outgoing data transmission. As an alternative or in addition, a standby mode for reception may also exist within a particular reception window at preset times in the therapeutic unit. If there is no incoming data transmission directed from the patient device to the implantable medical device within the response window or the reception window, then the implantable medical device shuts down its standby mode for reception again. It is possible in this way for an outgoing data transmission from the implantable medical device (i.e., the therapeutic unit) to the patient device to be answered with an incoming data transmission acknowledging receipt of the outgoing data transmission within a preselected response time window (reception time window). It is possible here to add more data to the incoming data transmission in addition to the pure acknowledgment signal.

The object of the invention is to make a follow-up examination (follow-up care examination) for a patient who has an implantable medical device, e.g., a cardiac pacemaker, as efficient as possible. On the occasion of a follow-up examination, the examining physician analyzes a series of data detected on the part of the implantable medical device, e.g., data on current stimulus thresholds for effective stimulation pulses in the case of a cardiac pacemaker, data on a natural (intrinsic) heart rate of the patient detected by the implantable medical device, data indicating how much voltage is required to stimulate the heart to contract, data on pulse properties, data on the charge status of the battery, data on the functionality of electrode lines connected to the implantable medical device and so forth.

According to this invention, this object is achieved by a therapeutic system having a therapeutic unit, i.e., in particular an implantable medical device such as a cardiac pacemaker or a defibrillator. The therapeutic unit comprises a control unit and a memory connected to the control unit as well as a telemetry unit connected at least indirectly to the control unit for wireless bidirectional transmission of data to and from an external device, e.g., to a patient device or directly to a service center. In addition, the therapeutic unit comprises a detection unit for detecting physiological data of a patient, e.g., the intrinsic heart rate, the prevailing stimulus threshold for electrostimulation, results of a retrograde conduction test and operational data on the therapeutic unit, reflecting, e.g., a prevailing stimulation pulse property, the functionality of electrode lines connected to the therapeutic unit or the status of the battery of the therapeutic unit.

The control unit of the therapeutic unit is designed to trigger an outgoing data transmission from the implantable therapeutic unit to an external device on the basis of preselected events internally within the treatment device, e.g., at points in time defined internally within the treatment device or on detection of certain preselected events. The control unit maintains a standby mode for reception on the part of the telemetry unit for receiving the beginning (header) of an incoming data transmission from the external device to the therapeutic unit exclusively within a preselected response time window after an outgoing data transmission from the implantable therapeutic unit to the external device or within a reception time window that is preselected in time.

It should be pointed out here that for the purposes of this description, the terms "incoming data transmission" and "outgoing data transmission" are used with respect to the implantable therapeutic unit. An outgoing data transmission in the sense of this description is thus a data transmission arriving at an external device or at the service center.

The therapeutic system is designed to add follow-up signaling data, signaling an imminent follow-up examination, to an incoming data transmission to be sent within the response time window or the reception time window. The control unit of the implantable therapeutic unit is designed to prompt the sensor unit at a preselected point in time to detect physiological data or operational data of the therapeutic unit required for a follow-up examination and to store it in the memory of the implantable therapeutic unit in response to receipt of an incoming data transmission containing follow-up signaling data. In addition, the control unit of the implantable therapeutic unit prompts the transmission of data collected in this way for a follow-up examination with a subsequent outgoing data transmission to the external device.

Such a therapeutic system offers several advantages. First, preliminary investigations prior to a follow-up examination to be ordered on the part of the implantable therapeutic device may be performed close in time before a follow-up examination, so that the data thereby compiled is up to date but then need not be determined during the actual follow-up examination. This saves valuable time during the actual follow-up examination. In addition, the automatic determination of the data required for the follow-up examination initiated in this way has the advantage that the required examinations are not forgotten, as may otherwise be the case, when the physician must trigger these examinations manually step by step (e.g., by means of a programming device), as has previously been the case on the occasion of a follow-up examination.

According to a first variant of an embodiment of the therapeutic system, the control unit of the implantable therapeutic unit is designed so that the preselected point in time at which the therapeutic unit orders the data to be compiled for the follow-up examination is immediately after receipt of the follow-up signaling data.

With this system, the therapeutic system preferably includes a service center which is designed for bidirectional data communication with the implantable therapeutic unit (optionally via an external device) and which triggers the sending of incoming data transmissions directed at the implantable therapeutic unit with follow-up signaling data at a preliminary examination point in time, at which the preliminary examinations are to be started for an imminent follow-up examination. To do so, the service center in the preferred variant of the embodiment has a date memory for storing the date of an imminent follow-up examination and is designed to calculate, based on the dates stored in the date memory, a preliminary examination point in time which is a preselected amount of time before the date stored in the date memory for a coming follow-up examination. The service center is also designed to order an incoming message containing follow-up signaling data as the response to an outgoing message from the therapeutic unit, which is received on the part of the service center or the patient device after the preliminary examination point in time determined previously. In this variant of the embodiment, the preliminary examination point in time is thus calculated in the service center.

As an alternative, the therapeutic system may also be designed so that the implantable therapeutic unit has a date and time transducer connected to the control unit; the control unit is designed to extract from follow-up signaling data a date of a coming follow-up examination in response to the receipt of such follow-up signaling data in order to then determine the point in time for a preliminary examination, which is set a preselected amount of time before the date of the coming follow-up examination. This point in time of the preliminary examination determined by the implantable therapeutic unit in this way is then stored in the memory of the implantable therapeutic unit. The control unit is also designed to prompt the sensor unit at the point in time for the preliminary examination as stored in the memory to detect the data required for the follow-up examination. In addition, the control unit then orders the transmission of this data with a following outgoing data transmission.

In this variant of the embodiment, the actual point in time of the preliminary examination is thus determined in the implantable therapeutic unit itself. Accordingly a service center as part of the therapeutic system is preferably designed so that it transmits the date of an imminent follow-up examination as soon as possible to the implantable therapeutic unit, i.e., not after the intended preliminary examination point in time has passed but instead already at a point in time when the next follow-up examination point in time has been set.

To determine a date for a follow-up examination, an input unit which is directly or indirectly connected to the service center and which allows input of a date of a coming follow-up examination is preferably provided. The input of such a date then results in the addition of follow-up signaling data to an incoming data transmission either after the preliminary examination point in time which is to be determined or shortly after input of the date for the follow-up examination.

In view of the fact that collection of the data required for a follow-up examination on the part of the implantable therapeutic unit, just like data transmission itself, requires a portion of the energy, which is available only to a limited extent, it is advantageous if either the implantable therapeutic unit is designed so that it allows collection of data as part of a preliminary examination to the follow-up examination only after preselected minimum intervals of time from a prior preliminary examination or the service center is designed so that it allows incoming data transmission containing follow-up signaling data only in certain minimum intervals. It is thus possible to prevent too many follow-up and preliminary examinations from being triggered and thus an unnecessarily great amount of energy being consumed.

In addition to the therapeutic system as a whole, an individual implantable therapeutic unit is also provided as a solution to the aforementioned task. This therapeutic unit differs from essentially known therapeutic units at least in that its control unit is designed to prompt the sensor unit at a preselected point in time to compile physiological data or operational data of the therapeutic unit required for a follow-up examination and store it in the memory of the implantable therapeutic unit in response to receipt of an incoming data transmission containing follow-up signaling data. In addition, the control unit is designed to order the transmission of this data with an outgoing data transmission after conclusion of the collection of the data. The special feature of such an implantable therapeutic unit thus consists of the fact that, on the basis of the design of its control unit, it is capable of detecting signaling data in an incoming data transmission, analyzing it suitably and then ordering the collection of physiological data and/or operational data of the implantable therapeutic unit.

According to another advantageous variant of the therapeutic unit, it is designed to cease from collecting data required for a follow-up examination at the point in time intended by the follow-up signaling data if the battery of the therapeutic unit has been drained below a preselected limit at this point in time.

An advantageous alternative variant of the therapeutic system consists of the fact that the therapeutic unit is set, optionally due to an incoming data transmission containing the corresponding follow-up signaling data, so that the therapeutic unit automatically triggers the collection of data needed for a follow-up examination at preselected intervals of time, preferably amounting to a few months.

Other advantageous embodiments of such an implantable therapeutic unit are derived from the preceding discussions of the therapeutic system.

BRIEF DESCRIPTION OF THE DRAWINGS

The invention will now be explained in greater detail on the basis of an exemplary embodiment with reference to the figures, in which.

DETAILED DESCRIPTION OF THE INVENTION

Figure 1:
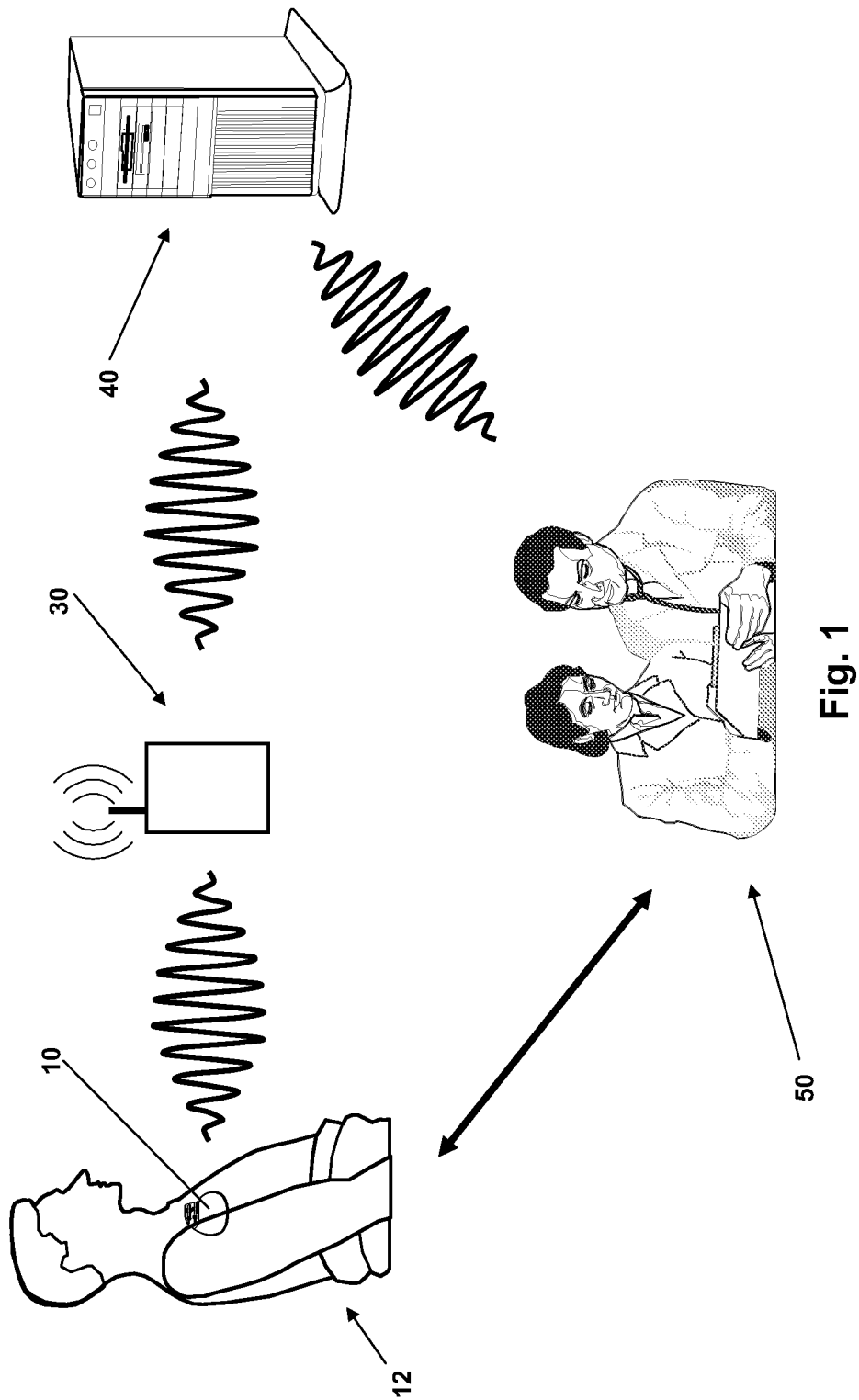
FIG. 1: shows a therapeutic system with an implantable therapeutic unit, an external device (patient device) and a service center.

The therapeutic system illustrated in FIG. 1 includes an implantable therapeutic unit 10, which in this case is a cardiac pacemaker implantable in a patient 12. Other components of the system include an external device 30 and a service center 40.

The external device 30—also known as the patient device—and the implanted therapeutic unit 10 are designed to exchange data bidirectionally by wireless transmission with a comparatively short range. Therefore, the external device 30 remains in the vicinity of the patient 12.

Furthermore, the external device 30 is designed to establish a bidirectional data link over a greater distance to a central service center 40, which is represented by a server in FIG. 1.

A physician 50 (or a team of physicians) has the opportunity to query data stored in the service center 40 for a specific implantable therapeutic unit. Furthermore, the service center 40 is designed so that it transmits messages regularly regarding a particular individual implantable therapeutic unit 10 or regarding the health status of the corresponding patient 12 to a physician 50, e.g., by means of SMS or e-mail. Conversely, the physician 50 has an opportunity to store data in the service center 40, e.g., data pertaining to the date of a fixed future care examination (follow-up examination) for the patient 12.

As part of such a follow-up examination, the physician 50 comes in direct contact with the patient 12 as indicated by the bidirectional arrow in FIG. 1. The physician 50 then has an opportunity to communicate directly bidirectionally with the implanted therapeutic unit 10 by means of a programming device (not shown). According to today's state of the art, data required for a follow-up examination is acquired by the physician himself during a follow-up examination by means of a programming device and the implantable therapeutic unit 10.

As already explained above in detail, the implantable therapeutic unit 10 is designed so that it automatically causes an outgoing data transmission to an external device 30 on the occasion of a preselected incident or at a preselected point in time and is ready to receive after conclusion of this data transmission for only a previously determined amount of time (a response time window) to receive the start (at least the header) of an incoming data transmission directed from the external device 30 to the implanted therapeutic unit 10. In the simplest case, this incoming data transmission consists exclusively of an acknowledgement, signaling to the implanted therapeutic unit 10 that the outgoing data transmission was successful, so that the implanted therapeutic unit 10 need not prompt a renewed outgoing data transmission containing the same data.

The bidirectional data link between the external device 30 and the service center 40 may be unlimited with regard to time and may be either wireless or hardwired because there is no shortage of resources on the transmission link between the external device 30 and the service center 40 like that with respect to the implantable therapeutic unit 10. Data received by the implantable therapeutic unit 10 is therefore usually transmitted immediately by the external device 30 to the service center 40. The service center 40 has the option of prompting an incoming data transmission with the implantable therapeutic unit 10, which may contain data going beyond an acknowledgement signal.

The follow-up signaling data in the special exemplary embodiment in particular, triggering the implantable therapeutic unit 10 on the basis of its concrete embodiment to begin, either immediately or at a calculated preliminary examination point in time, to collect physiological and/or operational data needed for a follow-up examination.

The therapeutic system depicted in FIG. 1 therefore allows the following scenario:

The service center offers the physician the option of storing the data of a planned follow-up examination with the service center.

At a desired point in time (depending on the scenario, with the next incoming data transmission which takes place in response to input of a follow-up examination date or only after a previously calculated preliminary examination point in time, the service center prompts the external device 30 to send an incoming data transmission containing follow-up signaling data of such a type that it triggers the implanted therapeutic unit to collect such data as is needed for a follow-up examination, either immediately or at a preliminary examination point in time, which is to be calculated by the implantable therapeutic unit itself. The prompting of the external device by the service center is to be understood here as meaning that the service center 40 triggers a data transmission containing the corresponding data to an external device 30 at a given point in time, i.e., at the point in time of the preliminary examination, for example, or immediately after the date has been set for a follow-up examination. The patient device 30 is therefore triggered to add the corresponding follow-up signaling data to the next possible incoming data transmission to the implantable therapeutic unit 10.

This incoming data transmission takes place as soon as the external device 30 has received an outgoing data transmission on the part of the implantable therapeutic unit 10.

After receipt of the corresponding incoming data transmission containing follow-up signaling data, the implantable therapeutic unit 10—more specifically, its control unit—prompts the collection of the corresponding data by, for example, triggering the measurement of the stimulus threshold, which is performed by measuring the intrinsic heart rate for a retrograde conduction test, transmitting the pulse properties, performing an electrode check or something similar.

The data thus determined is transmitted by the implantable therapeutic unit 10 with the next outgoing data transmission to the external device 30, which transmits this data further to the service center 40, where this data is then available to the physician 50 during a follow-up examination then to be performed.

Figure 2:
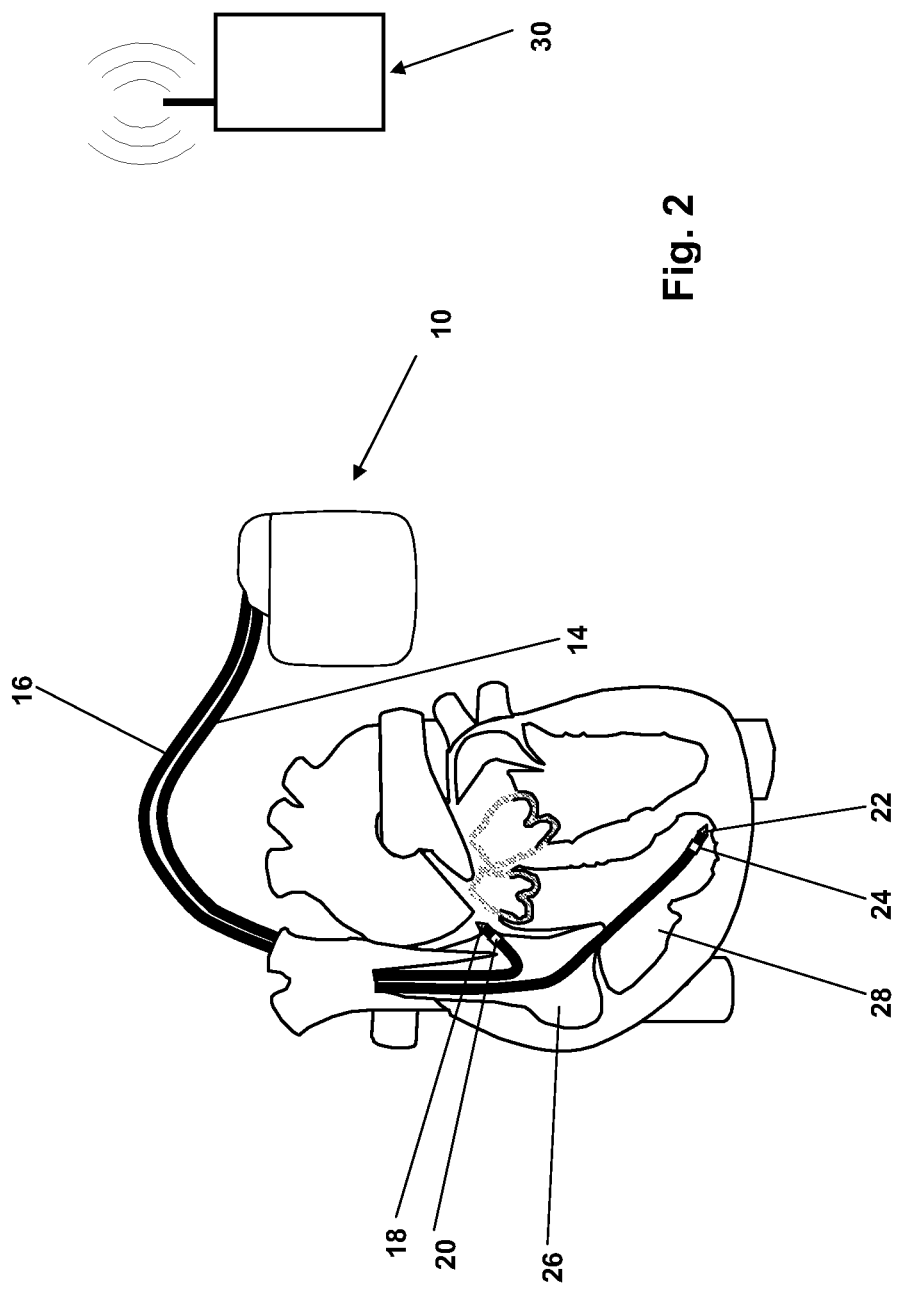
FIG. 2: shows a detailed diagram of the implantable therapeutic unit in the form of a dual-chamber cardiac pacemaker in combination with the patient device.
Figure 3:
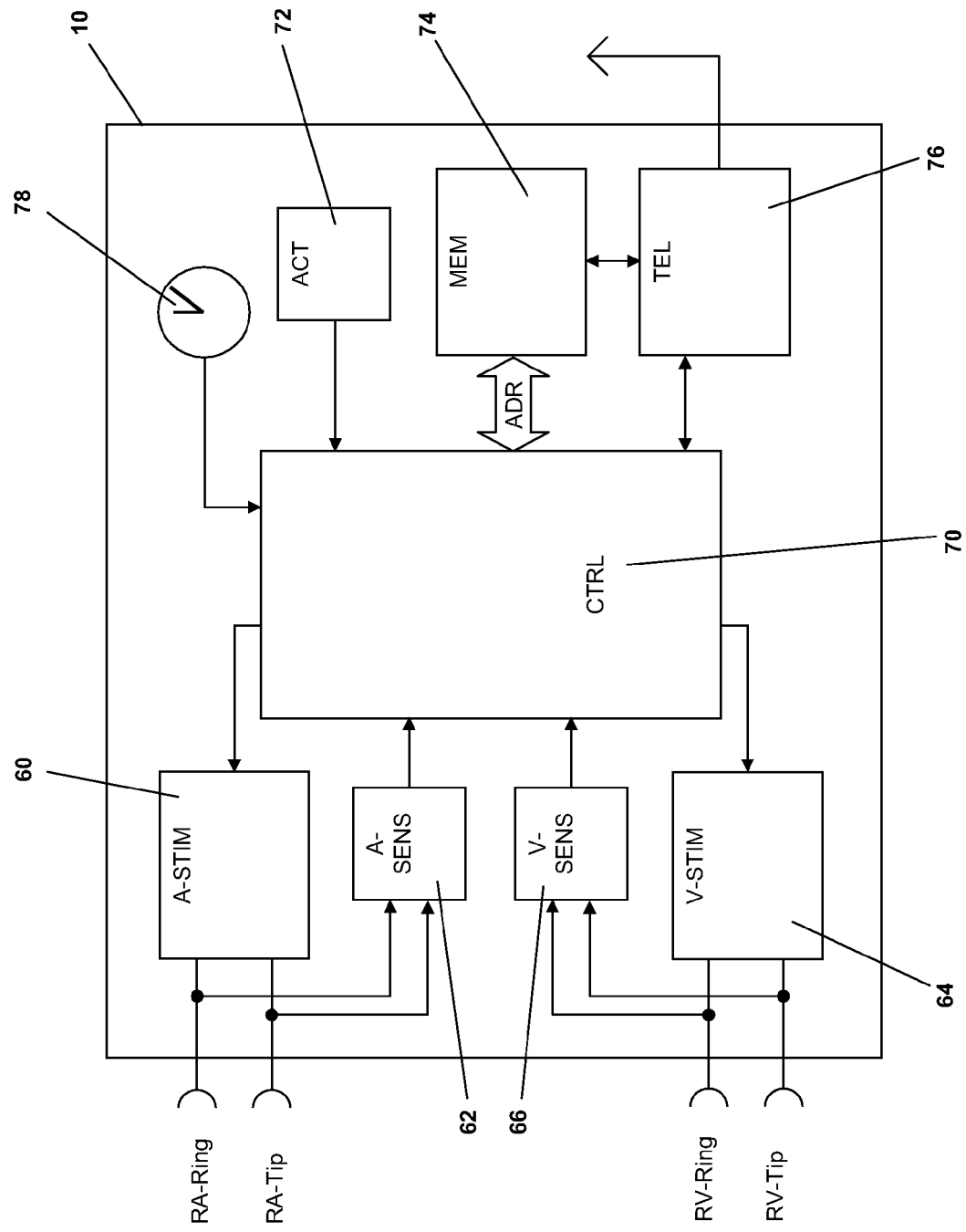
FIG. 3: shows a block diagram of the implantable therapeutic unit.

The implantable therapeutic unit is preferably an implantable medical device such as a cardiac pacemaker or a cardioverter/defibrillator. FIG. 2 shows a dual-chamber cardiac pacemaker as an implantable therapeutic unit 10. This dual-chamber cardiac pacemaker is connected to stimulation and sensing electrodes 18 and 20 and/or 22 and 24 in the atrium and/or in the ventricle of the heart via electrode lines 14 and 16, so that stimulation pulses can be delivered to the heart in this way and electric potentials can be received by the heart.

To do so, the electrode lines 14 and 16 are connected accordingly to an atrial stimulation unit 60, an atrial sensing unit 62, a ventricular stimulation unit 64 and a ventricular stimulation unit 66. These units are in turn connected to a central control unit 70 of the cardiac pacemaker 10. By means of the sensing units 62 and 66, the central control unit 70 of the cardiac pacemaker 10 is capable of detecting an intrinsic atrial or ventricular heart rate of a patient or determining the efficacy of an atrial or ventricular stimulation pulse delivered via one of the stimulation units 60 or 64 to thereby determine an atrial or ventricular stimulus threshold in an essentially known manner. In addition, the control unit 70 is connected to an activity sensor 72 to be able to adapt a respective stimulation rate to the hemodynamic demands of a patient.

In addition, the control unit 70 is connected to a memory 74, which may contain, first of all, control commands for the control unit 70 but may also serve as a memory for a patient's physiological data detected by means of the stimulation units 60 and 64 and the sensing units 62 and 66. Furthermore, the memory 74 serves as a buffer memory for a data transmission for which the memory 74 is connected to a telemetry unit 76. The telemetry unit 76 may also be connected directly and exclusively to the control unit 70. The control unit 70 controls the telemetry unit 76 in the manner described previously so that it prompts an outgoing data transmission in which data stored in the memory 74 is transmitted to the external device 30 and does so on detection of certain events, e.g., ventricular fibrillations or at certain points in time. The control unit 70 switches the telemetry unit 76 to receive for a brief response time window after the end of such an outgoing data transmission. When the telemetry unit 76 receives, within this response time window, the header of an incoming data transmission signaling to the control unit 70 that the incoming data transmission pertains to the dual-chamber cardiac pacemaker 10, then the standby mode for reception is maintained for the duration of this incoming data transmission and the reception is then deactivated. In this way, any amount of data may be added to an incoming data transmission, at least theoretically.

In the special exemplary embodiment described here, the control unit 70 is designed to respond to follow-up signaling data contained in an incoming data transmission in such a way that the control unit 70 immediately prompts the collection of data required for a follow-up examination or, alternatively, by the control unit 70 extracting the date of an imminent follow-up examination from the signaling data. With the help of this date, the control unit 70 then calculates a suitable preliminary examination point in time which comes before the date of the follow-up examination at which point in time the preliminary examinations must be initiated in order to be available for follow-up examination. With the help of a time and date transducer 78, the control unit 70 then triggers the collection of data required for the follow-up examination at the previously determined preliminary examination point in time.

In the preferred exemplary embodiment described here, the control unit 70 is designed to allow a repeat of the collecting of data for a follow-up examination only after preselected minimum intervals of time to rule out the possibility of depletion of the battery merely by collecting the data for a follow-up preliminary examination.

What is claimed is:

1. A therapeutic system comprising:
   an implantable therapeutic unit, comprising
      a control unit;
      a memory connected to the control unit;
      a telemetry unit connected at least indirectly to the control unit for wireless bidirectional transmission of data to and from an external device;
      a detection unit configured to detect physiological data of a patient or operational data of said implantable therapeutic unit;
      wherein the control unit is configured to trigger an outgoing data transmission from the implantable therapeutic unit to the external device based on preselected therapeutic-device-internal events and establish a standby mode for reception on part of the telemetry unit to receive a beginning portion or header of an incoming data transmission from the external device to the implantable therapeutic unit within a preselected response time window after the outgoing data transmission from the implantable therapeutic unit to the external device or within a reception time window at times preset in the implantable therapeutic unit;
      wherein said incoming data transmission comprises an acknowledgement configured to signal to the implanted therapeutic unit that the outgoing data transmission was successful such that a prompt for a renewed outgoing data transmission containing the data is not required;
      wherein said incoming data transmission further comprises follow-up signaling data that signals a coming or future time for a follow-up examination;
      wherein the control unit is also configured to prompt a sensor unit at a preselected point in time in response to receipt of the follow-up signaling data to detect detected data at said future time comprising preselected required physiological data or operational data of the implantable therapeutic unit for a follow-up examination and to store detected data in the memory at said future time without storing said detected data in the memory at time of programming and transmit the detected data together with a subsequent outgoing data transmission to the external device;
      wherein the implantable therapeutic unit has a time and date transducer connected to the control unit, and wherein the control unit is configured in response to receipt of follow-up signaling data, to extract from the follow-up data a date of a coming or future follow-up examination and to determine a point in time for a preliminary examination to occur a preselected amount of time before the extracted date for the coming follow-up examination, and wherein said control unit is configured to prompt the sensor unit at the point in time of the preliminary examination as the preselected point in time to detect the preselected required physiological data or operational data for the coming or future follow-up examination.

2. The therapeutic system according to claim 1, further comprising:
   a service center configured to communicate bidirectionally with the external device for data communication with the implantable therapeutic unit;
      wherein said service center has a date memory for storing a date for a coming follow-up examination;
      wherein said service center is configured to determine the point in time for the preliminary examination which occurs a preselected amount of time before the date for the coming or future follow-up examination;
      wherein said service center is configured to prompt the external device to generate an incoming message directed from the external device to the implantable therapeutic unit after receipt of an outgoing message originating from the implantable therapeutic unit after the point in time of the preliminary examination, said incoming message comprising the follow-up signaling data and wherein said incoming message is transmitted to the implantable therapeutic unit within the preselected response time window.

3. The therapeutic system according to claim 2, wherein the service center is designed to prompt the external device to transmit said incoming message within the preselected response time window to the implantable therapeutic unit when a preselected resting period of time has elapsed since a prior transmission of signaling data to the implantable therapeutic unit.

4. The therapeutic system according to claim 2, wherein the service center comprises, at least indirectly, an input unit for entering the date of an upcoming follow-up examination.

5. The therapeutic system according to claim 1, wherein the implantable therapeutic unit is designed to prompt the sensor unit to detect the preselected required physiological data or operational data of the implantable therapeutic unit for the follow-up examination and to store the detected data in the memory and to transmit the detected data with a subsequent outgoing data transmission to the external device only when more than a preselected dormant time has elapsed since a prior detection or transmission of data.

6. The therapeutic system according to claim 1, wherein the implantable therapeutic unit further comprises a battery, and is further configured to cease from detecting data required for the follow-up examination at the point in time intended by the follow-up signaling data if the battery of the implantable therapeutic unit has been drained below a preselected limit at this point in time.

7. The therapeutic system according to claim 1, wherein said therapeutic unit is further configured to automatically trigger the detection of data needed for a follow-up examination at preselected intervals of time, wherein said preselected intervals of time amount to a few months.

8. A therapeutic system comprising:
  an implantable therapeutic unit, comprising
    a control unit;
    a memory connected to the control unit;
    a telemetry unit connected at least indirectly to the control unit for wireless bidirectional transmission of data to and from an external device;
    a detection unit configured to detect physiological data of a patient or operational data of said implantable therapeutic unit;
    wherein the control unit is configured to trigger an outgoing data transmission from the implantable therapeutic unit to the external device based on preselected events internal to the implantable therapeutic unit and establish a standby mode for reception on part of the telemetry unit to receive a beginning portion or header of an incoming data transmission from the external device to the implantable therapeutic unit within a preselected response time window after the outgoing data transmission from the implantable therapeutic unit to the external device or within a reception time window at times preset in the implantable therapeutic unit;
    wherein said incoming data transmission comprises an acknowledgement configured to signal to the implanted therapeutic unit that the outgoing data transmission was successful such that a prompt for a renewed outgoing data transmission containing the data is not required;
    wherein said incoming data transmission further comprises follow-up signaling data that signals a coming future time for a follow-up examination;
    wherein the control unit is also configured to prompt a sensor unit at a preselected point in time to detect detected data comprising preselected required physiological data for a follow-up examination or operational data of the implantable therapeutic unit and to store detected data in the memory in response to the receipt of an incoming data transmission containing follow-up signaling data, and transmit the detected data to the external device together with a subsequent outgoing data transmission;
  a service center configured to communicate bidirectionally with the external device for data communication with the implantable therapeutic unit;
  wherein said service center is configured to store a point in time for a preliminary examination which occurs a preselected amount of time before the date for the coming follow-up examination;
  wherein said service center is configured to prompt the external device to generate an incoming message directed from the external device to the implantable therapeutic unit after receipt of an outgoing message originating from the implantable therapeutic unit after the point in time of the preliminary examination, said incoming message comprising the follow-up signaling data and wherein said incoming message is transmitted to the implantable therapeutic unit within the preselected response time window;
  wherein the service center is configured to prompt the external device to transmit said incoming message within the preselected response time window to the implantable therapeutic unit when a preselected resting period of time has elapsed since a prior transmission of signaling data to the implantable therapeutic unit;
  wherein the implantable therapeutic unit has a time and date transducer connected to the control unit, and wherein the control unit is configured in response to receipt of follow-up signaling data, to extract from the follow-up data a date of a coming or future follow-up examination and to determine a point in time for a preliminary examination to occur a preselected amount of time before the extracted date for the coming follow-up examination, and wherein said control unit is configured to prompt the sensor unit at the point in time of the preliminary examination as the preselected point in time to detect the preselected required physiological data or operational data for the coming or future follow-up examination; and
  wherein the implantable therapeutic unit is designed to prompt the sensor unit to detect the preselected required physiological data or operational data of the implantable therapeutic unit for the follow-up examination and to store the detected data in the memory and to transmit the detected data with a subsequent outgoing data transmission to the external device only when more than a preselected dormant time has elapsed since a prior detection or transmission of data.

9. The therapeutic system according to claim 8, wherein the implantable therapeutic unit further comprises a battery, and is further configured to cease from detecting data required for the follow-up examination at the point in time intended by the follow-up signaling data if the battery of the implantable therapeutic unit has been drained below a preselected limit at this point in time.

10. The therapeutic system according to claim 8, wherein said therapeutic unit is further configured to automatically trigger the detection of data needed for a follow-up examination at preselected intervals of time, wherein said preselected intervals of time amount to a few months.

* * * * *